United States Patent
Boye

(10) Patent No.: US 9,763,622 B2
(45) Date of Patent: *Sep. 19, 2017

(54) SENSOR ELEMENT WITH AN INSULATION LAYER

(71) Applicant: ST. JUDE MEDICAL COORDINATION CENTER BVBA, Zaventem (BE)

(72) Inventor: Shawn Boye, Menlo Park, CA (US)

(73) Assignee: ST. JUDE MEDICAL COORDINATION CENTER BVBA, Zaventem (BE)

(*) Notice: Subject to any disclaimer, the term of this patent is extended or adjusted under 35 U.S.C. 154(b) by 0 days.

This patent is subject to a terminal disclaimer.

(21) Appl. No.: 15/093,086

(22) Filed: Apr. 7, 2016

(65) Prior Publication Data

US 2016/0220187 A1    Aug. 4, 2016

Related U.S. Application Data

(62) Division of application No. 13/808,196, filed as application No. PCT/EP2011/060033 on Jun. 16, 2011, now Pat. No. 9,332,923.

(Continued)

(30) Foreign Application Priority Data

Jul. 6, 2010 (SE) ....................... 1050741

(51) Int. Cl.
*A61B 5/00* (2006.01)
*A61B 5/0215* (2006.01)
(Continued)

(52) U.S. Cl.
CPC .............. *A61B 5/6851* (2013.01); *A61B 5/01* (2013.01); *A61B 5/026* (2013.01); *A61B 5/0215* (2013.01);
(Continued)

(58) Field of Classification Search
CPC ..... A61B 5/6851; A61B 5/026; A61B 5/0215; A61B 5/02055; A61B 2562/12
See application file for complete search history.

(56) References Cited

U.S. PATENT DOCUMENTS 5,113,868 A    5/1992  Wise et al.
RE35,648 E    11/1997  Tenerz et al.
(Continued)

FOREIGN PATENT DOCUMENTS

EP    1 671 669 A1    6/2006
EP    2 163 190 A1    3/2010
(Continued)

OTHER PUBLICATIONS

Extended European Search Report dated May 13, 2016, 5 pgs.
(Continued)

*Primary Examiner* — Catherine Voorhees
(74) *Attorney, Agent, or Firm* — Foley & Lardner LLP

(57) ABSTRACT

A sensor element comprises a sensor section comprising a sensor unit configured to measure a physiological variable or any other signal in a living body and to generate a sensor signal in response to the variable or other signal, and a bond section comprising contact members configured to electrically connect at least one signal transmitting microcable. The bond section is coated with an electrically insulating material and the sensor unit is left uncoated. The sensor element may further comprise an intermediate section between the sensor section and the bond section. The intermediate section includes electric connection lines configured to connect the contact members to the sensor unit. The intermediate section is also coated with the electrically insulating material.

17 Claims, 6 Drawing Sheets

Related U.S. Application Data

(60) Provisional application No. 61/361,693, filed on Jul. 6, 2010.

(51) Int. Cl.
   | | | |
   |---|---|---|
   | *A61B 5/0205* | (2006.01) | |
   | *A61B 5/026* | (2006.01) | |
   | *A61B 5/01* | (2006.01) | |
   | *A61B 5/05* | (2006.01) | |

(52) U.S. Cl.
   CPC ............ *A61B 5/02055* (2013.01); *A61B 5/05* (2013.01); *A61B 2562/12* (2013.01); *Y10T 156/10* (2015.01)

(56) References Cited

U.S. PATENT DOCUMENTS

| | | |
|---|---|---|
| 5,701,905 A | 12/1997 | Esch |
| 5,902,248 A | 5/1999 | Millar et al. |
| 6,090,052 A | 7/2000 | Akerfeldt et al. |
| 6,167,763 B1 * | 1/2001 | Tenerz ................. A61B 5/0215 73/756 |
| 7,263,894 B2 | 9/2007 | Tenerz |
| RE39,863 E | 10/2007 | Smith |
| 7,343,811 B2 | 3/2008 | Tenerz et al. |
| 7,785,268 B2 | 8/2010 | Miethke et al. |
| 9,332,923 B2 * | 5/2016 | Boye ........................ A61B 5/01 |
| 2003/0028128 A1 | 2/2003 | Tenerz |
| 2003/0029245 A1 | 2/2003 | Izadnegahdar et al. |
| 2006/0129061 A1 * | 6/2006 | Kaneto ............. A61M 25/0043 600/561 |
| 2006/0207335 A1 * | 9/2006 | Tenerz ................. A61B 5/0215 73/754 |
| 2008/0132806 A1 * | 6/2008 | Smith .................... A61B 5/036 600/585 |
| 2009/0088650 A1 | 4/2009 | Corl |
| 2011/0196216 A1 | 8/2011 | Quarder et al. |
| 2013/0116528 A1 | 5/2013 | Boye |

FOREIGN PATENT DOCUMENTS

| | | |
|---|---|---|
| JP | 62-145780 A | 6/1987 |
| JP | 6-66621 A | 3/1994 |
| JP | H11-508160 A | 7/1999 |
| JP | 2000-287944 A | 10/2000 |
| JP | 2006-167119 A | 6/2006 |
| JP | 11-33004 A | 9/2006 |
| JP | 2006-231059 A | 9/2006 |
| JP | 2007-105459 A | 4/2007 |
| JP | 2008-539811 A | 11/2008 |

OTHER PUBLICATIONS

European Office Action dated Jan. 7, 2015, 4 pgs.
European Office Action dated Jan. 31, 2014, (4 pgs.).
Japanese Office Action and English language translation dated Feb. 25, 2014, (4 pgs.).
Japanese Office Action and English translation, May 16, 2017, 6 pages.

* cited by examiner

SENSOR ELEMENT WITH AN INSULATION LAYER

CROSS-REFERENCE TO RELATED APPLICATIONS

This application is a divisional application of U.S. application Ser. No. 13/808,196, filed Jan. 3, 2013, which is the National Stage of International Application No. PCT/EP2011/060033, filed Jun. 16, 2011, which claims priority to U.S. Provisional Application Ser. No. 61/361,693 and Swedish Application No. 1050741-6, both filed Jul. 6, 2010, the entire contents of all of which are incorporated herein by reference.

FIELD OF THE INVENTION

The present invention relates generally to sensor elements used in the medical field, and in particular to such sensor elements used in situ for intravascular measurements of physiological variables and other signals in a living body, and mounted at the distal end of a guide wire, and to methods of manufacture of such sensor elements.

BACKGROUND OF THE INVENTION

In many medical procedures, various physiological conditions present within a body cavity need to be monitored. These physiological conditions may be physical in their nature, such as pressure, temperature and flow velocity, and may provide the physician or medical technician with critical information as to the status of a patient's condition.

One arrangement that is widely used to monitor physiological conditions in a living body is a sensor wire comprising a sensor element, an electronic unit, a signal transmitting cable connecting the sensor element to the electronic unit, a flexible tube having the sensor element and the cable disposed therein, a solid metal wire (a so-called core wire) having a plurality of sections such that each of the sections has a different flexibility, and a coil that is attached to the distal end of the wire. The sensor element is often present in the form of a microchip, and the signal transmitting cable may be a microcable.

Furthermore, the sensor element may be arranged in a short tube, also referred to as a jacket or a sleeve. The jacket is hollow and accommodates besides the sensor element also a portion of a core wire and often at least one microcable. According to the prior art, the jacket is mainly used to protect the sensor element.

Such an arrangement may be used to determine the ability of a specific coronary vessel to supply blood to the heart muscle, by measuring the intracoronary pressure distally and proximally to a stenosis. The sensor element of such a pressure sensor often comprises a flexible membrane, and the two main types of such pressure sensors are absolute pressure sensors and differential or relative pressure sensors. In an absolute pressure sensor, the membrane is usually mounted across a small cavity wherein a reference pressure, usually vacuum pressure, exists, and the pressure to be measured acts on the opposing surface of the membrane. A differential pressure sensor measures the difference of two pressures acting on opposing sides of the membrane.

The movement or deformation of the membrane can be sensed in different ways by any kind of pressure sensitive element, such as by measuring the changes of electric characteristics of a piezoresistive body, the changes of resistance of an electric conductor or the change of capacitance of a suitably adapted capacitor, which is coupled to the membrane, and which thereby reaches varied forced or strained states as a reaction to any movement of the membrane.

Furthermore, a temperature sensitive resistor may be mounted in the vicinity of the pressure sensitive element, which temperature sensitive resistor has a known temperature dependence, for recording temperature. An electric circuit may also be included, which selectively transfers signals from either of the pressure sensitive element and the temperature sensitive resistor.

Several different designs of sensor wires are known in the prior art, and examples of such sensor wires are described in U.S. Pat. No. 6,167,763 B1 and RE35648 E1, disclosing the complete sensor wire, and RE39863, which discloses an arrangement having a "double" Wheatstone bridge. The content of said patent publications is hereby incorporated by reference for the methods and devices disclosed therein.

U.S. Pat. No. 5,113,868 relates to a catheter system including one or several capacitive pressure sensors having a silicon diaphragm. Prior to assembly of the catheter system, the pressure sensors are partially encapsulated with a biomedically compatible material to seal off the hollow cylindrical interiors of the catheter sections from bodily fluids.

U.S. Pat. No. 5,701,905 describes a guide catheter including a sensor element for measurement of blood pressure, and mentions that protective material may be used to maintain the sensor away from the artery walls and to allow the sensor to be directly exposed to blood.

Currently, as described in the above-referenced U.S. Pat. No. 6,167,763 B1, the entire sensor element of the sensor wire assembly is embedded in a soft, elastic material, such as silicone rubber. This protects the sensor element from mechanical impact by surrounding structures while still exposing the membrane to a medium (blood) having the ability to transfer pressure changes, such that the membrane will detect such changes in the fluid passing in the vessel in which the sensor is situated. Further, an embedded sensor is not exposed to blood or other fluids, which potentially could cause short-circuiting in the electric circuits. Thus, the silicone material, e.g. Silicone Dow Corning 734, also functions as an insulator to minimise so-called wet insulation failure.

To comply with The American National Standard for Blood pressure transducers (ANSI/AAMA BP22) each sensor wire is tested for signal stability. Preferably, the assembly must not exhibit more than 5.5 mmHg/h signal deviation under constant conditions. Sensor wires that exceed the above limit should preferably be failed for drift, and this is one of the most common causes of failure during production. Until now, the cause of drift has not been fully understood, and one object of the present invention is to achieve an improved sensor element with regard to signal stability.

SUMMARY OF THE INVENTION

The above-mentioned object is achieved by the present invention as described herein. For example, the present invention relates to a sensor element (1), which comprises a sensor section (2) comprising a sensor unit (3) configured to measure a physiological variable or any other signal in a living body and to generate a sensor signal in response to said variable or other signal, a bond section (5) comprising contact members configured to electrically connect at least one signal transmitting microcable, wherein the bond section is coated with an electrically insulating material (18)

and the sensor section is left uncoated. The sensor element may further comprise an intermediate section between said sensor section and said bond section, including electric connection lines (19) configured to connect the contact members to the sensor unit, which intermediate section is also coated with said electrically insulating material. The invention further relates to a sensor wire and a method of producing a sensor element.

According to the present invention, a sensor element is disclosed that provides stable, linear measurements and that reduces the drift failure rate to 1±1%.

Thus, the object is achieved by a sensor element, which comprises a sensor section comprising a sensor unit configured to measure a physiological variable or any other signal in a living body and to generate a sensor signal in response to said variable or other signal, a bond section comprising contact members configured to be electrically connected to at least one signal transmitting microcable, wherein the bond section is coated with an electrically insulating material and the sensor section is left uncoated.

According to a preferred embodiment of the invention, the sensor element further comprises an intermediate section between said sensor section and said bond section, including electric connection lines configured to connect the contact members to the sensor unit.

Preferably, essentially the entire intermediate section is also coated with said electrically insulating material.

According to another embodiment of the invention, a sensor wire is provided. The sensor wire has a proximal region, a distal sensor region and a distal tip region, and comprises a sensor element according to the present invention, a jacket accommodating at least a part of said sensor element, which is attached to a core wire, and at least one signal transmitting microcable, which is connected to said sensor element and running along the sensor wire.

According to another embodiment of the invention there is provided a method of producing a sensor element. The method comprises providing a sensor support body, forming a sensor section comprising forming a sensor unit, forming a bond section comprising forming contact members, and coating the bond section with an electrically insulating material while the sensor section is left uncoated.

In a preferred embodiment of the invention, said method further comprises forming an intermediate section between said sensor section and said bond section.

Preferably, said method further comprises coating essentially the entire intermediate section with said electrically insulating material.

Consequently, the present invention discloses a sensor element, which is coated with an electrically insulating material from its proximal end to a location proximal to a sensor section. In other words, a sensor element is described, wherein the bond section, and optionally also an intermediate section, is coated with an electrically insulating material, provided that the sensor section is not coated. Thus, the sensor section will not be electrically insulated. Consequently, the sensor unit will be free from electrically insulating material, and thus will be directly accessible to the fluid medium in the living body, in which the measurement of a physiological variable or any other signal is to be performed.

The present invention is based upon the novel finding of what causes the above-mentioned problem of signal deviation and drift. Currently, as mentioned above, the membrane and possible passive and active resistors comprised by a sensor element are embedded with silicone. However, this silicone layer has an uneven thickness (see FIG. 4), which results in a variable three dimensional stress state that, when wetted, can be described in terms of Hooke's Law:

$$\sigma_{ij} = c_{ijkl} \epsilon_{kl}$$

where $\sigma_{ij}$, $c_{ijkl}$ and $\epsilon_{kl}$ are the stress, stiffness and strain tensors, respectively. Application of silicone insulation on the membrane and on the passive and active resistors thereby influences the signal stability and increases the failure rate during production. Extrapolated to the clinical environment, the prevailing application of silicone may affect the accuracy of the measurement of physiological variables and any other signals in the living body, such as pressure measurements in the coronary artery.

Further, when using a sensor wire provided with a sensor element, it is highly desirable that the measurements to be performed, e.g. pressure measurements, almost immediately generate a valid and accurate signal. One substantial factor in this regard is that effective wetting of the sensor unit is achieved. By leaving the sensor section free from electrically insulating material in accordance with the present invention, the sensor unit will be directly accessible to the fluid medium in the living body, in which the measurements are to be performed. Consequently, the present invention also facilitates an effective wetting of the sensor unit.

SHORT DESCRIPTION OF THE APPENDED DRAWINGS

In the figures, identical reference signs designate identical, or essentially identical, technical features.

DETAILED DESCRIPTION OF PREFERRED EMBODIMENTS OF THE INVENTION

Throughout the application, the word "distal" refers to a part located further away in respect of the operator, and the word "proximal" refers to a part located closer to the operator.

Figure 1:
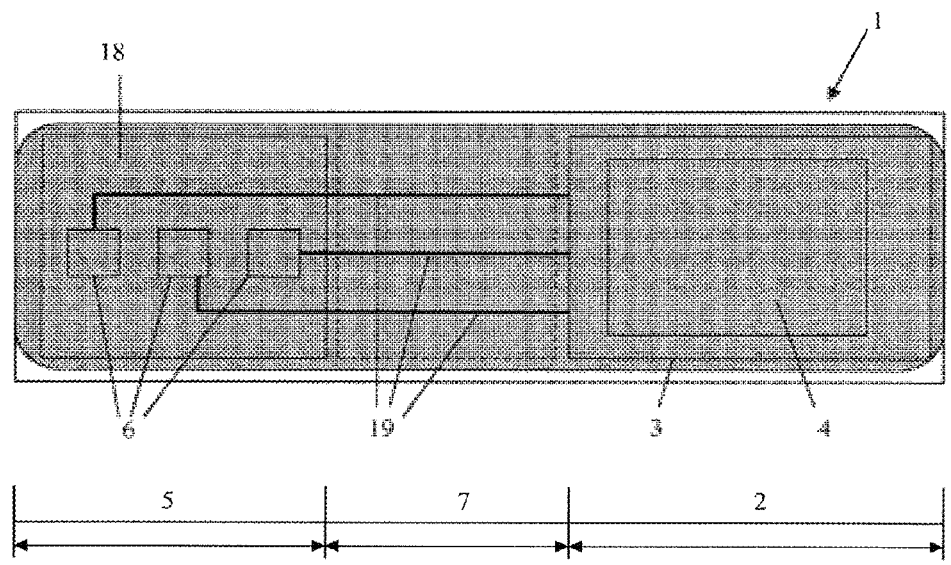
FIG. 1 is a schematic top view of a sensor element according to the prior art.

FIG. 1 illustrates a top view of a sensor element 1 according to the prior art. The sensor element 1 comprises a sensor section 2 and a bond section 5 comprising contact members 6 (e.g. three contact members, as illustrated in the figure) configured to be electrically connected to at least one signal transmitting microcable. The sensor element 1 further comprises an intermediate section 7 between said sensor section 2 and said bond section 5, including electric connection lines 19 configured to connect the contact members 6 to the sensor unit 3. The sensor section 2 comprises the sensor unit 3 which is configured to measure a physiological variable or any other signal in a living body and to generate a sensor signal in response to said measurement. The sensor unit 3 comprises a membrane 4. The entire sensor element 1 is coated with an electrically insulating material 18 (as illustrated by a narrow-striped area).

Figure 2:
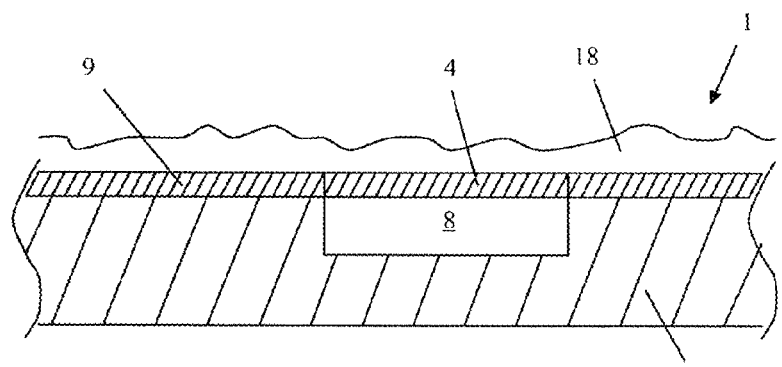
FIG. 2 is a schematic side view of a sensor element according to the prior art.

FIG. 2 illustrates a side view of a sensor element 1 according to the prior art. The sensor element 1 comprises a sensor support body 17, in which a cavity 8 has been formed, e.g. by etching. Further, a layer 9 covers the cavity 8, thereby forming a reference chamber with a membrane 4. The entire sensor element 1 is coated with an electrically insulating material 18 having an uneven thickness, which results in the drift problem as discussed above.

Figure 3:
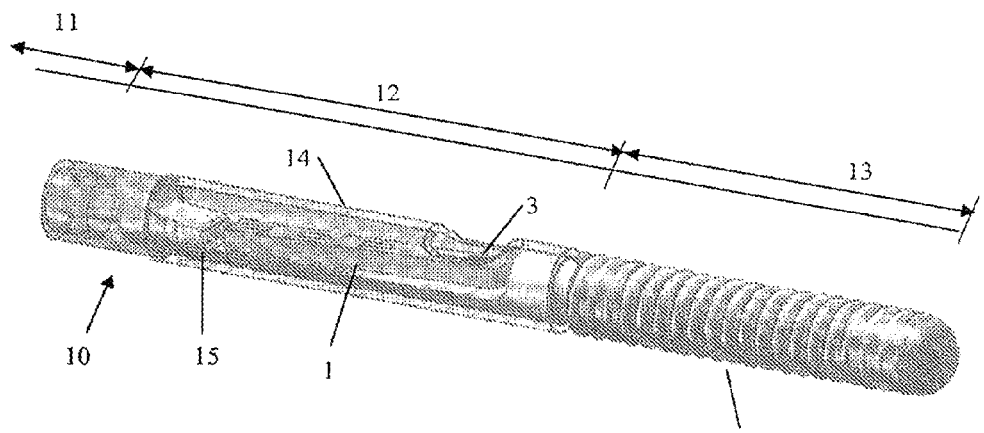
FIG. 3 shows the general design of a sensor wire according to the prior art.
Figure 11:
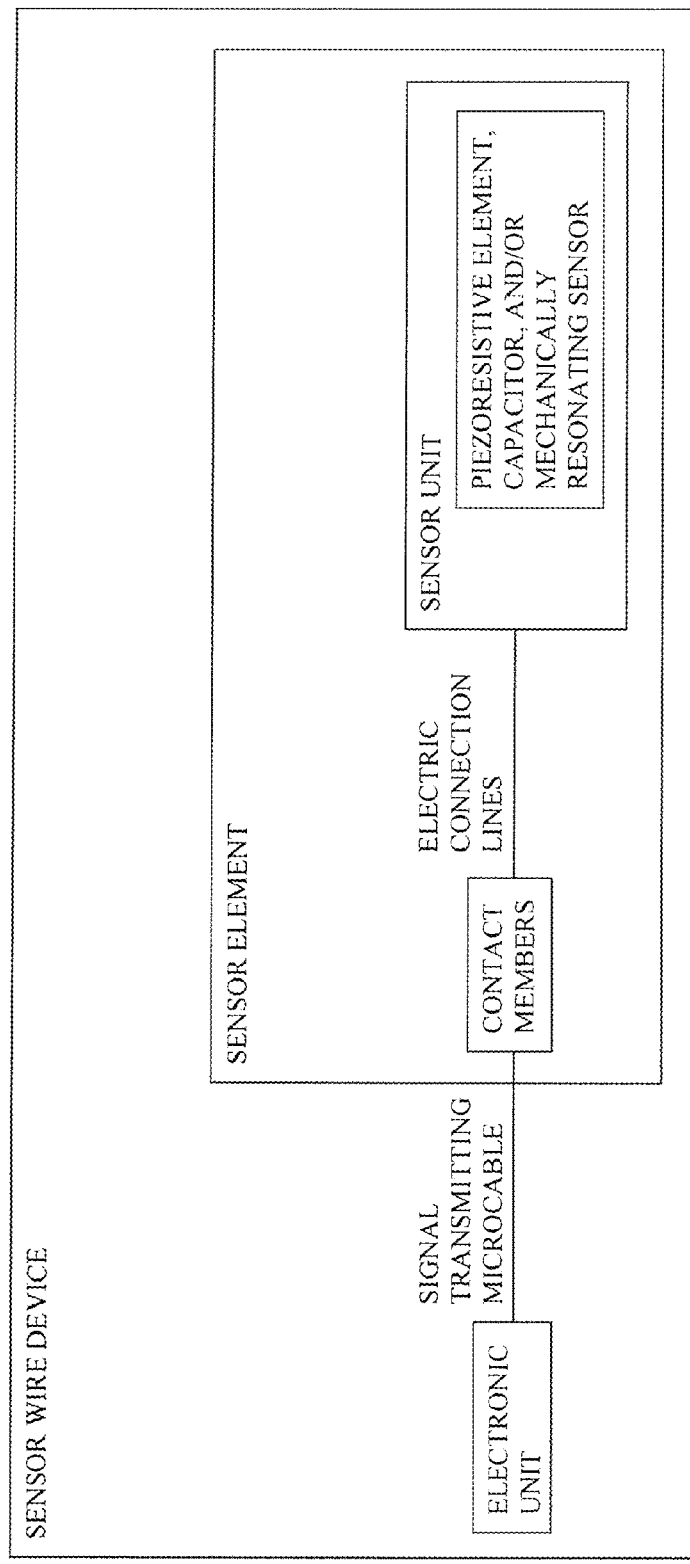
FIG. 11 is a schematic view of a sensor wire device according to an embodiment of the invention.

FIG. 3 illustrates a sensor wire 10 according to the prior art. The sensor wire 10 has a proximal region 11, a distal sensor region 12 and a distal tip region 13. It comprises a core wire 15, a sensor element 1 with a sensor unit 3, a jacket 14 and a coil 16. The core wire extends through the jacket 14 and into the coil 16. The sensor element 1, comprising the sensor unit 3, is mounted on the core wire 15 within the jacket 14, and is connected to an electronic unit (shown in FIG. 11) via one or several microcables (shown in FIG. 11) that run along the sensor wire 10.

Figure 4:
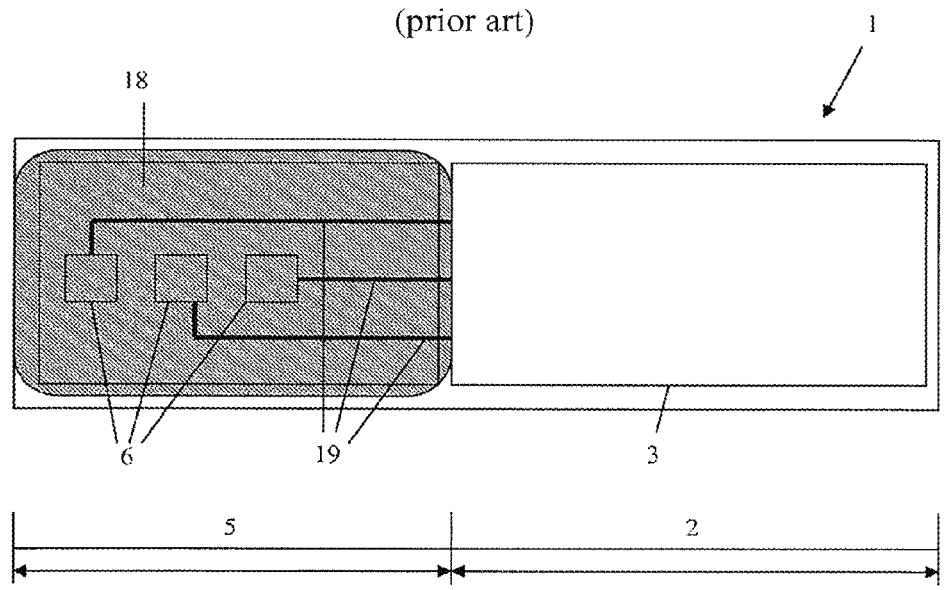
FIG. 4 is a schematic top view of a sensor element according to the invention, wherein a bond section is coated with an electrically insulated material.

FIG. 4 illustrates a top view of a sensor element 1 according to the invention. The sensor element 1 comprises a sensor section 2 and a bond section 5 comprising contact members 6 (e.g. three contact members, as illustrated in the figure) configured to be electrically connected to at least one signal transmitting microcable. The sensor section 2 comprises a sensor unit 3 which is configured to measure a physiological variable or any other signal in a living body and to generate a sensor signal in response to said measurement. According to the invention, the bond section 5 is coated with an electrically insulating material 18 and the sensor section 2 is left uncoated.

Figure 5:
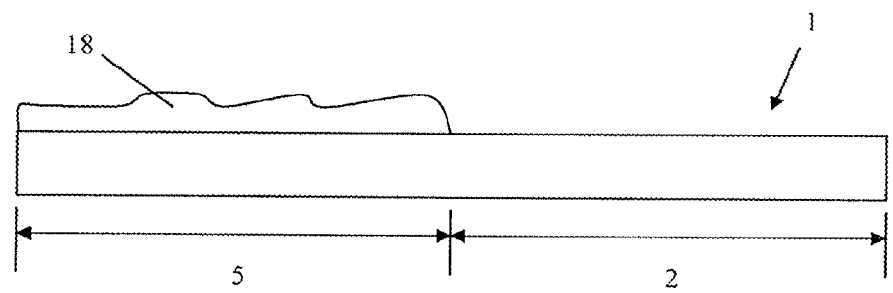
FIG. 5 is a schematic side view of a sensor element according to the invention, wherein a bond section is coated with an electrically insulated material.

FIG. 5 shows a side view of a sensor element 1 according to the invention, wherein a bond section 5 is coated with an electrically insulating material 18 and a sensor section 2 is left uncoated.

Figure 6:
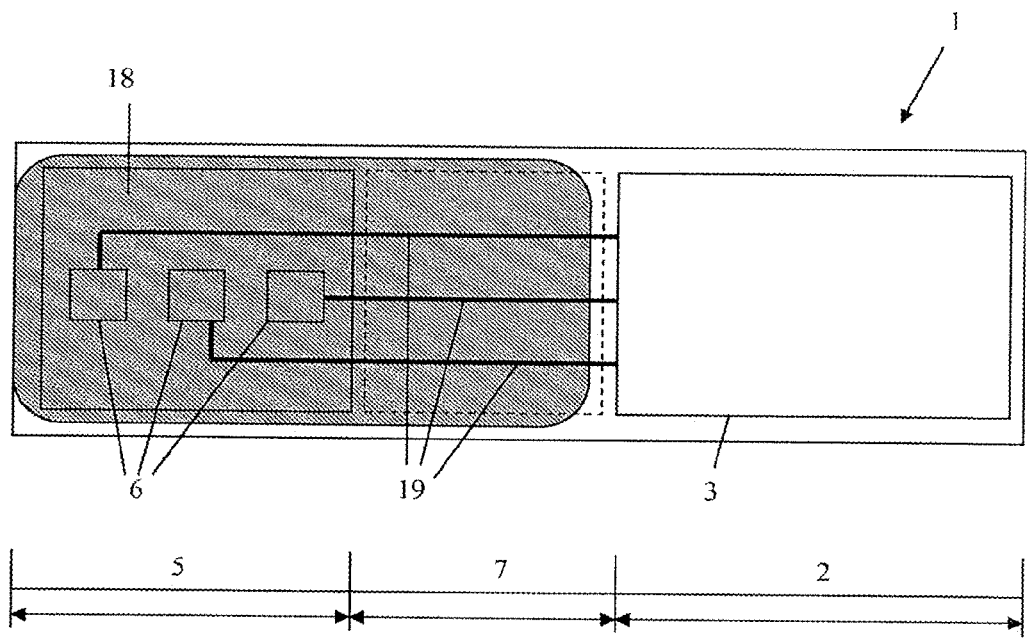
FIG. 6 is a schematic top view of a sensor element according to a preferred embodiment of the invention, wherein a bond section and an intermediate section are coated with an electrically insulated material.

FIG. 6 illustrates a top view of a sensor element 1 according to a preferred embodiment of the invention. The sensor element 1 comprises a sensor section 2 and a bond section 5 comprising contact members 6 (e.g. three contact members, as illustrated in the figure) configured to be electrically connected to at least one signal transmitting microcable. The sensor element 1 further comprises an intermediate section 7 between said sensor section 2 and said bond section 5, including electric connection lines 19 configured to connect the contact members 6 to the sensor unit 3. The sensor section 2 comprises a sensor unit 3 which is configured to measure a physiological variable or any other signal in a living body and to generate a sensor signal in response to said measurement. According to this preferred embodiment of the invention, the bond section 5 and essentially the entire surface of the intermediate section 7 are coated with an electrically insulating material 18 and the sensor section 2 is left uncoated.

Figure 7:
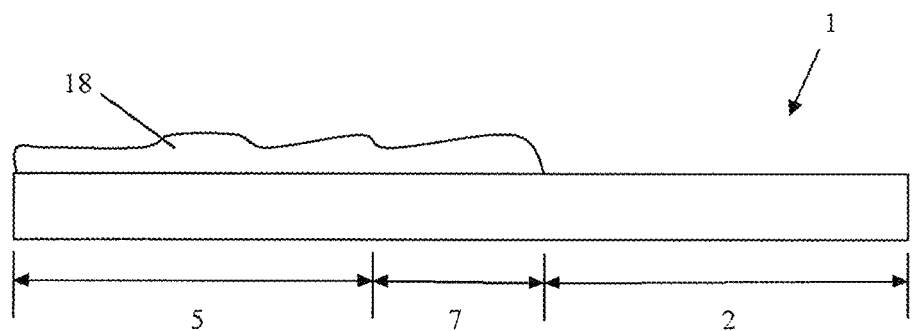
FIG. 7 is a schematic side view of a sensor element according to a preferred embodiment of the invention, wherein a bond section and an intermediate section are coated with an electrically insulated material.

FIG. 7 shows a side view of a sensor element 1 according to a preferred embodiment of the invention, wherein a bond section 5 and essentially the entire surface of an intermediate section 7 are coated with an electrically insulating material 18 and a sensor section 2 is left uncoated.

Preferably, said electrically insulating material 18 is biocompatible and chemically stable in the living body.

Said electrically insulating material 18 may be selected from the group consisting of silicone or epoxy.

In one embodiment of the invention, said sensor element 1 has an elongated rectangular shape.

In one embodiment of the invention, said sensor element 1 has a maximum extension in the interval of 1.0-2.2 mm, a width in the interval of 0.1-0.6 mm, and a thickness in the interval of 0.05-0.3 mm.

In a preferred embodiment, said sensor element 1 has a maximum extension of 1.32 mm, and preferably has a width of approximately 0.16 mm and a thickness of approximately 0.09 mm.

In another embodiment of the invention, said sensor element 1 has a quadratic, spherical or elliptic shape.

Said sensor section 2 is sensitive to one or many physiological variables, such as pressure, temperature, and flow velocity.

Said sensor unit 3 may comprise at least one of a piezoresistive element, a capacitor, or a mechanically resonating sensor.

In one embodiment, said sensor unit 3 comprises at least one piezoresistive element (not shown in figure) arranged in connection with said membrane 4.

Such a piezoresistive element may be disposed on the upper surface of the membrane. Alternatively, it may be positioned underneath the membrane.

In one embodiment, said sensor unit 3 comprises a piezoresistive element and a temperature sensitive resistor (not shown).

In a preferred embodiment, said piezoresistive element is part of a first Wheatstone bridge of a sensor circuit, and said temperature sensitive resistor is part of a second Wheatstone bridge of the sensor circuit.

In one embodiment, the sensor unit 3 comprises a piezoresistive element arranged in connection with said membrane 4, and the sensor element 1 further comprises a group of resistors, wherein the piezoresistive element and the group of resistors in combination form a Wheatstone bridge (not shown).

Figure 8:
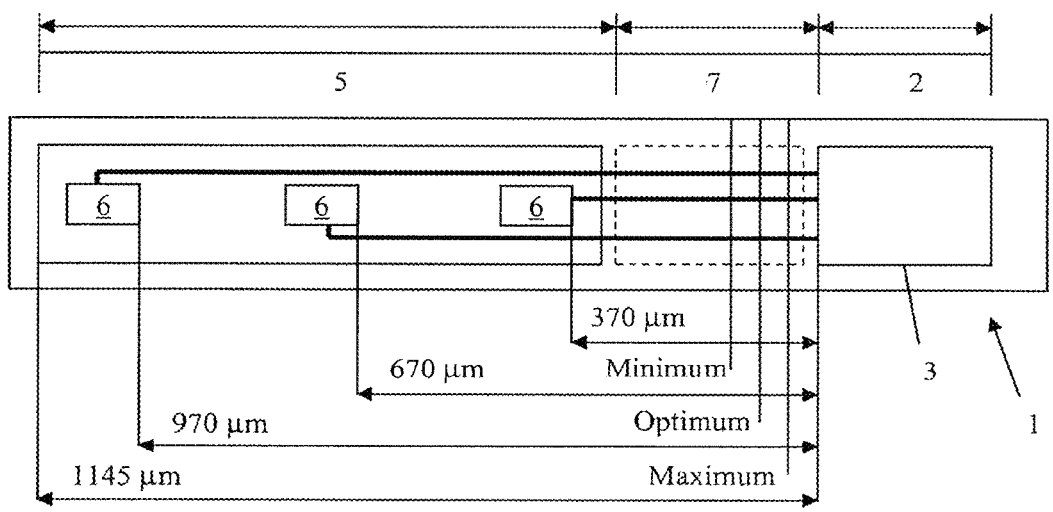
FIG. 8 shows a top view of a sensor element having a minimal, optimal and maximal section, respectively, which according to the invention is coated with an electrically insulating material.

FIG. 8 depicts a top view of a sensor element 1 comprising a sensor section 2, a bond section 5 and, according to a preferred embodiment of the invention, an intermediate section 7. A sensor unit 3 and three contact members 6 are depicted. From the proximal end of the sensor unit 3 (i.e. the left side of the sensor unit 3 as shown in the figure) to the distal end of the first contact member 6 (closest to the sensor unit 3), the distance is between 250 μm and 500 μm, preferably 350-400 μm and most preferably 370 μm. From the proximal end of the sensor unit 3 to the distal end of the second contact member 6, the distance is between 550 μm and 800 μm, preferably around 650-700 μm and most preferably 670 μm. From the proximal end of the sensor unit 3 to the distal end of the third contact member 6, the distance is between 850 μm and 1100 μm, preferably 950-1000 μm and most preferably 970 μm. From the proximal end of the sensor unit 3 to the proximal end of the bond section 5, the distance is between 1000 μm and 1400 μm (provided that said distance is larger than the distance from the proximal end of the sensor unit 3 to the distal end of the third contact member 6), more preferably 1100-1200 μm and most preferably 1145 μm.

According to the invention, the entire bond section 5 is coated with an electrically insulating material. In addition, essentially the entire intermediate section 7 is coated with the electrically insulating material. In FIG. 8, three border lines are depicted, specifying the minimal, optimal and maximal section, respectively, counted from the proximal end of the bond section 5, which according to the invention is coated with an electrically insulating material. From FIG. 8 it can be seen that the border lines specifying said minimal, optimal and maximal sections are all located proximally the sensor section 2, and thus the sensor section 2 will be left uncoated.

Figure 9:
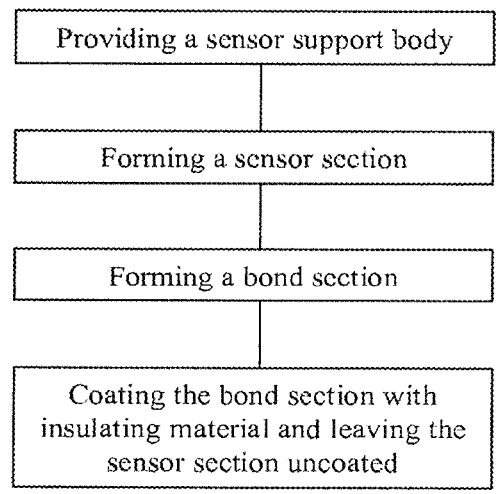
FIG. 9 depicts a method of producing a sensor element according to the present invention.

The present invention also relates to a method of producing a sensor element 1, which is illustrated by the diagram of FIG. 9. The method comprises providing a sensor support body, forming a sensor section, comprising forming a sensor unit; forming a bond section, comprising forming contact members; and coating the bond section with an electrically insulating material while the sensor section is left uncoated.

In one embodiment, said method of producing a sensor element 1 comprises configuring the sensor unit to measure a physiological variable or any other signal in a living body and to generate a sensor signal in response to said variable or other signal; and further comprises forming a cavity in said sensor support body, e.g. by etching, and bonding a layer to the sensor support body to cover the cavity, thereby forming a reference chamber with a membrane. Further, said bond section is formed proximal to the sensor section, and said contact members are configured to electrically connect at least one signal transmitting microcable.

Figure 10:
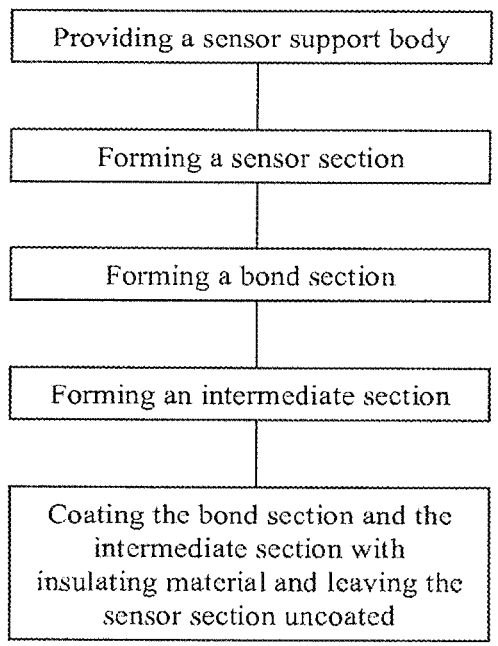
FIG. 10 shows a method of producing a sensor element according to a preferred embodiment of the present invention.

FIG. 10 shows a preferred embodiment of the method, further comprising forming an intermediate section between said sensor section and said bond section. The method further comprises coating said intermediate section with said electrically insulating material.

In one embodiment of the invention, said sensor support body 17 consists of silicon. Said layer 9 may consist of silicon, polycrystalline silicon, or monocrystalline silicon.

In one embodiment of said method, the forming of the sensor unit 3 comprises forming at least one of a piezoresistive element, a capacitor, or a mechanically resonating sensor.

In one embodiment of said method, the forming of the sensor unit 3 comprises arranging a piezoresistive element in connection with the membrane 4.

The present invention is not limited to the above-described preferred embodiments. Various alternatives, modifications and equivalents may be used. Therefore, the above embodiments should not be taken as limiting the scope of the invention, which is defined by the appending claims.

The invention claimed is:

1. A sensor element, comprising:
   a sensor support body;
   a sensor unit disposed on the sensor support body, the sensor unit being configured to measure a variable in a living body and to generate a sensor signal in response to said measurement, and the sensor unit comprising a cavity covered by a membrane;
   a plurality of contact members disposed on an upper surface of the sensor support body, the contact members being configured to be electrically connected to at least one signal transmitting microcable;
   a plurality of electric connection lines disposed on the upper surface of the sensor support body and connecting the respective contact members to the sensor unit and
   an electrically insulating layer that (i) coats an entirety of upper surfaces of the contact members, at least a portion of each electric connection line, and a portion of the upper surface of the sensor support body that surrounds the contact members and the coated portions of the electric connection lines, and (ii) does not coat a surface of the membrane.

2. The sensor element according to claim 1, wherein the sensor element has an elongated rectangular shape.

3. The sensor element according to claim 1, wherein the sensor element has a length in a range of 1.0 to 2.2 mm, a width in a range of 0.1 to 0.6 mm, and a thickness in a range of 0.05 to 0.3 mm.

4. The sensor element according to claim 1, wherein a material of the electrically insulating layer is biocompatible and chemically stable in the living body.

5. The sensor element according to claim 1, wherein a material of the electrically insulating layer is selected from a group consisting of silicone and epoxy.

6. The sensor element according to claim 1, wherein said sensor unit is sensitive to one or more physiological variables comprising pressure, temperature, and flow velocity.

7. The sensor element according to claim 1, wherein the sensor unit comprises at least one of a piezoresistive element, a capacitor, or a mechanically resonating sensor.

8. The sensor element according to claim 1, wherein the sensor unit comprises at least one piezoresistive element arranged in connection with the membrane.

9. A sensor wire for an intravascular measurement of a variable in a living body, wherein the sensor wire has a proximal region, a distal sensor region and a distal tip region, the sensor wire comprising:
   a sensor element according to claim 1 and arranged in the distal sensor region;
   a jacket accommodating at least a part of the sensor element;
   a core wire; and
   the at least one signal transmitting microcable connected to the contact members and running along the sensor wire.

10. A method of producing a sensor element, the method comprising:
   forming a sensor unit on a sensor support body, the step of forming the sensor unit comprising:
      forming a cavity in a sensor support body, and
      bonding a membrane to the sensor support body to cover the cavity,
      wherein the sensor unit is configured to measure a variable in a living body and to generate a sensor signal in response to said measurement;
   forming a plurality of contact members on an upper surface of the sensor support body, the contact members being configured to be electrically connected to at least one signal transmitting microcable;
   forming a plurality of electric connection lines on the upper surface of the sensor support body so as to connect the respective contact members to the sensor unit; and
   forming an electrically insulating layer that (i) coats an entirety of upper surfaces of the contact members, at least a portion of each electric connection line, and a portion of the upper surface of the sensor support body that surrounds the contact members and the coated portions of the electric connection lines, and (ii) does not coat a surface of the membrane.

11. The method according to claim 10, wherein the sensor element has an elongated rectangular shape.

12. The method according to claim 10, wherein the sensor element has a length in a range of 1.0 to 2.2 mm, a width in a range of 0.1 to 0.6 mm, and a thickness in a range of 0.05 to 0.3 mm.

13. The method according to claim 10, wherein a material of the electrically insulating layer is biocompatible and chemically stable in the living body.

14. The method according to claim 10, wherein a material of the electrically insulating layer is selected from a group consisting of silicone and epoxy.

15. The method according to claim 10, wherein said sensor unit is sensitive to one or more physiological variables comprising pressure, temperature, and flow velocity.

16. The method according to claim 10, wherein the sensor unit comprises at least one of a piezoresistive element, a capacitor, or a mechanically resonating sensor.

17. The method according to claim 10, wherein the sensor unit comprises at least one piezoresistive element arranged in connection with the membrane.

\* \* \* \* \*